US012773124B2

(12) United States Patent
Bilen-Rosas et al.

(10) Patent No.: US 12,773,124 B2
(45) Date of Patent: *Oct. 27, 2026

(54) SYSTEM AND METHOD FOR MONITORING AIRFLOW IN A TRACHEA WITH ULTRASOUND

(71) Applicant: Wisconsin Alumni Research Foundation, Madison, WI (US)

(72) Inventors: Guelay Bilen-Rosas, Middleton, WI (US); Humberto Gerardo Rosas, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 26 days.

This patent is subject to a terminal disclaimer.

(21) Appl. No.: 18/513,190

(22) Filed: Nov. 17, 2023

(65) Prior Publication Data

US 2024/0341625 A1 Oct. 17, 2024

Related U.S. Application Data

(63) Continuation of application No. 16/334,267, filed as application No. PCT/US2017/052233 on Sep. 19, 2017, now Pat. No. 11,819,322.

(Continued)

(51) Int. Cl.
*A61B 5/087* (2006.01)
*A61B 5/00* (2006.01)

(Continued)

(52) U.S. Cl.
CPC ............ *A61B 5/087* (2013.01); *A61B 5/7267* (2013.01); *A61B 5/7405* (2013.01); *A61B 5/742* (2013.01);

(Continued)

(58) Field of Classification Search
None
See application file for complete search history.

(56) References Cited

U.S. PATENT DOCUMENTS 6,537,228 B1 3/2003 Lambert
7,116,810 B2 10/2006 Miller et al.

(Continued)

FOREIGN PATENT DOCUMENTS

AU 2004222800 A1 11/2004
CN 100528078 C 8/2009

(Continued)

OTHER PUBLICATIONS

Granges et al., "Study of fetal tracheal fluid velocities using Doppler ultrasound," (Oct. 19, 2009), European Journal of Obstetrics & Gynecology and Reproductive Biology 148 (2010) 141-143. (Year: 2009).*

(Continued)

*Primary Examiner* — Keith M Raymond
*Assistant Examiner* — Ashish S. Jasani
(74) *Attorney, Agent, or Firm* — Quarles & Brady LLP

(57) ABSTRACT

Described here are systems and methods for monitoring airflow changes in a patient's airway during a medical procedure or as a general patient monitoring tool. Doppler ultrasound signals are acquired from the tracheal wall of the patient and parameters from those Doppler ultrasound signals are compared to baseline parameters. When a threshold change is detected, an alarm can be provided to a user to indicate respiratory compromise, which can include early airway compromise or airway obstruction.

9 Claims, 6 Drawing Sheets

Related U.S. Application Data

(60) Provisional application No. 62/396,339, filed on Sep. 19, 2016.

(51) Int. Cl.
*A61B 5/08* (2006.01)
*A61B 5/085* (2006.01)
*A61B 8/00* (2006.01)
*A61B 8/08* (2006.01)

(52) U.S. Cl.
CPC ................ *A61B 5/746* (2013.01); *A61B 8/08* (2013.01); *A61B 8/469* (2013.01); *A61B 8/488* (2013.01); *A61B 5/0816* (2013.01); *A61B 5/085* (2013.01); *A61B 5/4821* (2013.01)

(56) References Cited

U.S. PATENT DOCUMENTS

| | | | |
|---|---|---|---|
| 2006/0081255 | A1 | 4/2006 | Miller et al. |
| 2013/0289401 | A1 | 10/2013 | Colbaugh et al. |
| 2014/0039313 | A1 | 2/2014 | Palti |
| 2015/0164433 | A1 | 6/2015 | Halperin et al. |
| 2015/0209001 | A1 | 7/2015 | Wolf et al. |
| 2015/0216509 | A1 | 8/2015 | Yamagata et al. |
| 2015/0316520 | A1 | 11/2015 | Maguire et al. |

FOREIGN PATENT DOCUMENTS

| | | | |
|---|---|---|---|
| CN | 103417184 | A | 12/2013 |
| CN | 104254283 | A | 4/2018 |
| WO | 2015166485 | A1 | 11/2015 |

OTHER PUBLICATIONS

Brooks et al., "Relationship between lung vol. and tracheal area as assessed by acoustic reflection", (Mar. 1988), J Appl Physiol (1985), Mar. 1988;64(3): 1050-4. (Year: 1988).*
Bae et al., "Usefulness of ultrasound for selecting a correctly sized uncuffed tracheal tube for paediatric patients," (Nov. 2011), Anaesthesia, Nov. 2011;66(11):994-8. (Year: 2011).*
American Hospital Association The migration of care to non-hospital settings: have regulatory structures kept pace with changes in care delivery? TrendWatch, Jul. 2006. http://www.aha.org/research/reports/tw/twjuly2006migration.pdf.
Arlotto, Philippe et al. "An ultrasonic contactless sensor for breathing monitoring." Sensors (Basel, Switzerland) vol. 14,8 15371-86. Aug. 20, 2014, doi: 10.3390/s140815371 (Year: 2014).
Bae HK, et al. Cardiovascular screening in asymptomatic adolescents with metabolic syndrome. J Cardiovasc Ultrasound. 2015;23:10-19.
Barker, S. J., et al.(1997). The effects of motion on the performance of pulse oximeters in volunteers (revised publication). Anesthesiology, 86(1), 101.
Bhananker Sm, Posner KL, Cheney FW, Caplan RA, Lee LA, Domino KB. Injury and liability associated with monitored anesthesia care: a closed claims analysis. Anesthesiology 2006; 104: 228-34.
Brunke SS, et al. An ultrasound research interface for a clinical system. IEEE Trans Ultrason Ferroelectr Freq Control. 2007;54(1):198-210.
Chapelon, J., et al. (2000). New piezoelectric transducers for therapeutic ultrasound. Ultrasound In Medicine & Biology, 26(1), 153-159. http://dx.doi.org/10.1016/s0301-5629(99)00120-9.
Cullen KA, et al. Ambulatory surgery in the United States, 2006. US Department of Health and Human Services, Centers for Disease Control and Prevention, National Center for Health Statistics; Jan. 28, 2009, Revised Sep. 2009.
Kristensen, Ultrasonography in the Management of the Airway, Acta Anaesthesiologica Scandinavica, 2011, 55:1155-1173.
Lee, Helen H., et al. "Trends in death associated with pediatric dental sedation and general anesthesia." Pediatric Anesthesia 23.8 (2013): 741-746.
Mackenzie et al. Are ambulatory surgical patients as healthy as we think? Using a self-reported health status questionnaire to identify unsuspected medical comorbidities. Hss J. 2006;2(2): 121-6.
Mamie C, et al. Incidence and risk factors of perioperative respiratory adverse events in children undergoing elective surgery. Paediatr Anaesth. 2004;14(3):218-24.
Mason, K. P. "Challenges in paediatric procedural sedation: political, economic, and clinical aspects." British journal of anaesthesia 113.suppl_2 (2014): ii48-ii62.
Nagueh SF, et al. Doppler tissue imaging: A noninvasive technique for evaluation of left ventricular relaxation and estimation of filling pressures. Journal of the American College of Cardiology. 1997;30:1527-1533.
Nagueh SF, et al. Hemodynamic determinants of the mitral annulus diastolic velocities by tissue Doppler. Journal of the American College of Cardiology. 2001;37:278-285.
Palti, Yoram, et al. "Pulmonary Doppler signals: a potentially new diagnostic tool." European Journal of Echocardiography 12.12 ( 2011): 940-944. (Year: 2011).
Philips, HD11 XE Echocardiography System, Product Brochure, Copyright 2008 Koninklijke Philips Electronics NV., 12 pages.
Reeder et al., Use of Doppler Techniques (Continuous-Wave, Pulsed-Wave, and Color Flow Imaging) in the Noninvasive Hemodynamic Assessment of Congenital Heart Disease, Mayo Clinic Proceedings, 1986, 61:725-744.
Sheahan CG, et al. Monitoring and delivery of sedation. British Journal of Anaesthesia 113 (S2):ii37-ii47, 2014.
Singh, M., et al. (2010). Use of sonography for airway assessment an observational study. Journal of Ultrasound in Medicine, 29(1), 79-85.
Sohn DW, et al. Assessment of mitral annulus velocity by Doppler tissue imaging in the evaluation of left ventricular diastolic function. Journal of the American College of Cardiology. 1997;30:474-480.
Urman Rd, et al. Improving patient safety in the office: the Institute for Safety in Office-Based Surgery. APSF Newsl. 2011;26(1):3-4.
Vivier et al., "Diaphragm ultrasonography to estimate the work of breathing during non-invasive ventilation," (Apr. 5, 2012), Intensive Care Med (2012) 38:796-803. (Year: 2012).
International Search Report and Written Opinion dated Dec. 11, 2017 from Parent Application PCT/US17052233, 15 pages.

* cited by examiner

SYSTEM AND METHOD FOR MONITORING AIRFLOW IN A TRACHEA WITH ULTRASOUND

CROSS-REFERENCE TO RELATED APPLICATIONS

This application is a continuation of U.S. application Ser. No. 16/334,267, filed Mar. 18, 2019, which application is a 371 U.S. National Phase application of PCT/US2017/052233, filed Sep. 19, 2017, which claims the benefit of U.S. Provisional Patent Application Ser. No. 62/396,339, filed on Sep. 19, 2016, and entitled "SYSTEM AND METHOD FOR MONITORING AIRFLOW IN A TRACHEA WITH ULTRASOUND," which applications are herein incorporated by reference in their entireties.

BACKGROUND

In the past few decades, advances in monitoring technology have contributed to a heightened sense of safety during medical procedures. Despite technological advancements and improved anesthetic agents leading to an increased safety profile of anesthesia and sedation, morbidity and mortality rates remain high in spontaneously breathing patients. One of the primary reasons morbidity and mortality rates remain high is the delayed detection of early respiratory compromise, which impedes the timely implementation of rescue measures. The end results of respiratory compromise is insufficient oxygen to the brain and heart, leading to grave consequences including permanent neurological and cardiac damage, or even death. Currently available monitoring devices and techniques continue to be ineffective at measuring subtle airflow changes in the early stages of respiratory compromise.

Respiratory compromise may include one or more of the following scenarios: alterations in respiratory rate, decreased effort, obstruction in the upper airway anatomy (e.g., tongue obstruction, tissue obstruction, vocal cord spasms), or alterations in lower airway structures (e.g., bronchospasm, pneumonia). Patients under sedation can experience decreased respiratory effort and varying degrees of tissue laxity, which can lead to airway obstruction and both of which are difficult to assess.

Because of the lack of reliable respiratory monitoring, early recognition of respiratory compromise relies heavily on clinical expertise. Accurately monitoring for respiratory compromise is especially difficult in pediatric patients, whose anatomy makes maintaining airway and respiratory homeostasis challenging during inhalation induction for anesthesia or sedation. The head and neck anatomy of pediatric patients, as well their unique respiratory physiology, predisposes this patient population to a higher incidence of airway obstruction and rapid rate of desaturation. For example, pediatric patients experience higher rates of tongue obstruction during sedation and anesthesia due to their larger tongue size. Additionally, at baseline, pediatric patients have two- to three-fold higher oxygen consumption; decreased functional capacity leading to diminished oxygen reserves once apneic; decreased type-1 muscle fibers resulting in faster respiratory fatigue during times of labor; and a closing capacity that is at the level of tidal volume breathing.

Any loss in the degree of respiratory effort brought about by sedation/anesthesia or respiratory illness will tip the balance from staying stable and ventilating appropriately to quick ventilatory compromise, respiratory deterioration with decrease in airflow, and desaturation (i.e., type-2 respiratory failure). Unrecognized and delayed respiratory support requiring skilled airway maneuvers (e.g., hand-bag-ventilation) will lead to severe desaturation followed by bradycardia, which can be fatal for the patient.

As mentioned above, the currently available methods for monitoring respiratory compromise are ineffective at directly measuring airflow changes in non-intubated patients, thereby rendering the methods unreliable for accurately and timely detecting early respiratory compromise.

One of the most common methods currently employed for monitoring airflow is measuring end-tidal carbon dioxide ("CO2"). However, measuring end-tidal CO2 has inherent limitations because it is an indirect measurement of alterations in airflow and becomes increasingly inaccurate in non-intubated patients due to the lack of a closed circuit. As a consequence, the measured data are difficult for the practitioner to interpret in spontaneously breathing patients, which often leads to delays in the treatment of early airway compromise.

Another common method for monitoring for respiratory compromise is pulse oximetry, which indirectly measures a patient's oxygen saturation and which is a standard American Society of Anesthesiologists ("ASA") monitor in operating rooms and most office-based sedation cases. However, pulse oximetry does not directly monitor respiration and hence does not monitor ventilation. For example, an obstructed airway will decrease oxygen flow and hence oxygen supply to the body, leading to desaturation (i.e., a drop in oxygen). The limitation of pulse oximetry is a delayed response to desaturation, resulting in a time lag in the detection of hypoxic events, particularly in the presence of supplemental oxygen.

Electrocardiography ("ECG") monitoring, a non-respiratory monitor, can also be used, but only shows changes in heart rate (e.g., bradycardia) once arterial oxygen desaturation has exceeded a critical point. Thus, like end-tidal CO2 and pulse oximetry, ECG only indirectly measures respiratory compromise by displaying changes in heart function (e.g., drop in blood pressure and heart rate) due to decreased oxygen supply to the heart as the consequence of airflow deterioration. Moreover, ECG-monitoring does not provide real-time measurements necessary to timely identify early airway compromise.

Thoracic impedance monitoring can also be used for post-operative respiratory rate assessment. This measurement technique, however, is very susceptible to erroneous readings secondary to motion artifact. For instance, this methodology will continue to record a respiratory rate despite the patient breathing against a closed glottis, a situation in which airflow has ceased partially or completely.

Presently, the success of early detection of respiratory compromise relies heavily on physician expertise. A non-invasive method of quantifying small changes in airflow patterns would allow physicians with various degrees of experience to detect early respiratory compromise, specifically in the outpatient setting where sedation is delivered by non-anesthesiologists; in the ICU where pain management, particularly with opioids, can lead to over-sedation; in the post-anesthesia recovery unit where patients are still awakening from anesthesia; in the emergency room where patients are presenting with respiratory issues due to trauma, reactive airway exacerbations, or infection; and in the operating room for inhalation and intravenous induction.

Thus, there remains a need for a non-invasive system and method for directly and timely monitoring for respiratory compromise and airflow changes in patients. Such a system and method would be advantageous not only for clinical and outpatient settings, but for research and teaching applications, too. Such a tool would prompt timely airway rescue and reduce the morbidity and mortality rates associated with undetected respiratory compromise.

SUMMARY OF THE DISCLOSURE

The present disclosure overcomes the aforementioned drawbacks by providing systems and methods for non-invasively monitoring airflow in a subject's trachea using ultrasound.

It is an aspect of the present disclosure to provide a method for monitoring airflow in a trachea using an ultrasound system. A region-of-interest that includes a tracheal wall of a subject is selected. Doppler ultrasound signals are acquired from the region-of-interest and are provided to a computer system. Baseline signal data are also provided to the computer system. A parameter of the Doppler ultrasound signals is compared to a similar parameter in baseline signal data using the computer system. The computer system is then used to identify when the parameter of the acquired Doppler ultrasound signals differs from the similar parameter of the baseline signal data by a selected threshold amount. An alarm is provided to a user when the parameter of the acquired Doppler ultrasound signals is identified as differing from the similar parameter of the baseline signal data by the selected threshold amount.

It is another aspect of the present disclosure to provide an airway monitor that includes an ultrasound transducer, an acquisition system, a processor, and an alarm. The ultrasound transducer is adapted to acquire Doppler ultrasound signals from a tracheal wall of a subject. The acquisition system receives Doppler ultrasound signals from the ultrasound transducer and communicates those Doppler ultrasound signals to the processor. The processor compares the Doppler ultrasound signals to baseline data and identifies when a parameter of the acquired Doppler ultrasound signals differs from a similar parameter of the baseline signal data by a selected threshold amount. The alarm provides an auditory alarm, a visual alarm, or both, when the parameter of the acquired Doppler ultrasound signals is identified as differing from the similar parameter of the baseline signal data by the selected threshold amount.

The foregoing and other aspects and advantages will appear from the following description. In the description, reference is made to the accompanying drawings that form a part hereof, and in which there is shown by way of illustration a preferred embodiment. This embodiment does not necessarily represent the full scope of the invention, however, and reference is made therefore to the claims and herein for interpreting the scope of the invention.

DETAILED DESCRIPTION

Figure 1:
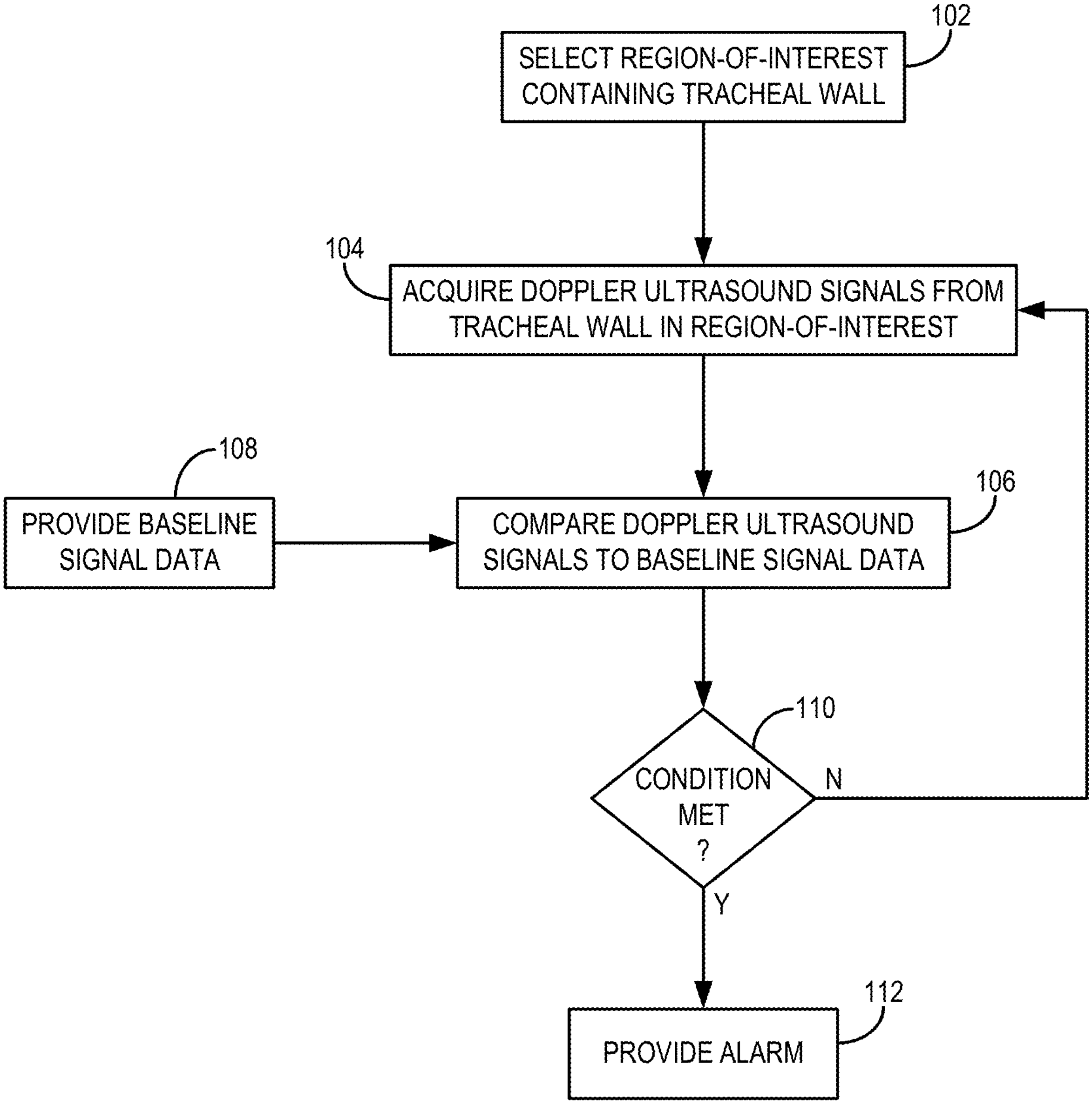
FIG. 1 is a flowchart setting forth the steps of an example method for monitoring for airflow changes by measuring Doppler ultrasound signals from a patient's tracheal wall.

Described here are systems and methods for monitoring airflow changes in a subject's airway. This monitoring may be performed during or prior to a procedure, or may be used as a general patient monitoring tool. For example, the systems and methods of the present disclosure can be used to monitor signs of airway obstruction or respiratory compromise during timeframes where patients have ongoing or residual sedation or anesthetics in their system. The systems and methods can also be implemented for quantitatively measuring airflow and related parameters. As one example, the systems and methods of the present disclosure can be used to quantitatively measure respiratory rate.

Currently, no device reliably measures airflow directly, continuously, and instantly. Presently available monitors display information for respiratory ventilation via indirect measurements (e.g., via measuring changes in CO2 and O2). These currently available monitors do not provide direct quantitative measurements of airflow and perform inaccurately in spontaneously breathing patients. Moreover the data provided by these currently available monitors is very delayed, and therefore these monitors often cannot timely detect early airway compromise.

The systems and methods described here utilize Doppler ultrasound to measure changes in the tracheal wall during inspiration and expiration. Doppler ultrasound is conventionally used to measure blood flow or the flow of other liquids, such as cerebrospinal fluid. It is a discovery of the present disclosure that Doppler ultrasound signals recorded from the tracheal wall, however, can be used to monitor airflow. By comparing properties of this Doppler signal to a baseline signal, respiratory compromise, such as airflow obstruction, can be identified. As an example, respiratory compromise can be identified as a percent decrease in Doppler signal amplitude relative to the baseline signal. The systems and methods described in the present disclosure thus provide a direct, real-time measurement of airflow that can be monitored to detect respiratory compromise, such as airway obstruction.

During anesthesia, especially in pediatric anesthesia, the systems and methods described in the present disclosure can provide an accurate monitor for airway obstruction and early respiratory comprise, leading to more timely intervention and reduced patient morbidity and mortality. The systems and methods described in the present disclosure can also provide an efficient teaching tool in the training of residents and fellows. For example, the measured values from this non-invasive monitor can be more tangibly correlated with clinical changes of the patient, which currently is not possible. Learning these clinical skills for the pediatric population otherwise requires many years of pediatric anesthesia practice. A teaching tool that can expedite this learning process would be advantageous.

The ultrasound-based monitor described in the present disclosure provides a method for detecting alterations in airflow using Doppler signaling along the tracheal wall. In some embodiments, pulsed wave Doppler techniques can be implemented. In some other embodiments, continuous wave Doppler techniques can be implemented. The non-invasiveness and continuous and instant collection of data makes this tool advantageous for collecting and displaying information about the changing dynamics of airflow in real-time. The systems and methods described in the present disclosure can therefore improve clinical judgment, practice, and teaching.

Referring now to FIG. 1, a flowchart is illustrated as setting forth the steps of an example method for monitoring a subject for respiratory compromise using ultrasound. The method includes selecting a region-of-interest ("ROI") containing the subject's trachea, as indicated at step 102. For example, the ROI can be selected by operating the ultrasound system to acquire B-mode images of the subject and identifying an ROI in those B-mode images that includes the subject's trachea. In some instances, the ROI can be selected manually. In some other instances, the ROI can be selected on an automatic or semi-automatic basis based on the hyperechoic nature of the tracheal wall in a B-mode image.

Doppler ultrasound signals are then acquired from the ROI using the ultrasound system, as indicated at step 104. Additionally, ultrasound imaging data can also be acquired during this time. Preferably, the Doppler ultrasound signals and imaging data are acquired while the ultrasound transducer is oriented such that the tracheal wall is being imaged in the longitudinal plane. The Doppler ultrasound signals, which include velocity data, and ultrasound imaging data are preferably continuously recorded while being analyzed to monitor for airway obstruction or respiratory compromise. In some embodiments, power Doppler imaging can be used, in which case the Doppler ultrasound signals may also, or alternatively, include amplitude data (e.g., the total strength of the measured Doppler shift).

As one example, pulsed wave Doppler ultrasound can be used to detect airflow changes across the trachea; however, continuous wave Doppler can also be used. It is a discovery of the present disclosure that velocities along the tracheal wall measured using pulsed wave Doppler correspond to airflow changes in spontaneously breathing and non-intubated patients. Thus, measured changes in the velocities along the tracheal wall can be associated with airflow changes, including airway obstruction or respiratory compromise. It is another discovery of the present disclosure that the amplitude of the power Doppler signals measured using power Doppler imaging along the tracheal wall can also be associated with airflow changes, including airway obstruction or respiratory compromise.

In one non-limiting example, the tracheal wall can be imaged in the longitudinal plane using a high-resolution ultrasound transducer (e.g., a 10-15 MHz transducer). Pulsed wave Doppler data obtained from the tracheal wall can be used to quantify tissue movement along the tracheal wall during the different phases of ventilation. It is a discovery of the present disclosure that increased pulse wave tissue Doppler velocities can be measured during inspiration and expiration, with the mean values changing with differences in airflow.

In some examples, Doppler ultrasound signals are continuously recorded from the ROI while the subject is breathing under anesthesia, sedation, or both. During breathing, changes in airflow in the trachea will be recorded as changes in the measured Doppler ultrasound signals, which can be compared to baseline data that were acquired before the subject was placed under anesthesia, sedation, or both. A suitable correlation or other algorithm can be used to identify critical changes in the subject's airflow, relative to the baseline data, in real-time, as described below.

In some other examples, the Doppler ultrasound signals can be compared to normative data in addition to, or in alternative to, baseline data. Such normative data may include data associated with expected normal airflow in a healthy patient, such as expected normal airflow velocities in a healthy patient. As one example, this normative data can be provided from a database of measured, normal airflow, which may have been reported in previous clinical or scientific studies. In examples where the Doppler ultrasound signals are compared to normative data, the suitable correlation or other algorithm can be used to identify critical changes in the subject's airflow relative to the normative data. By comparing the Doppler ultrasound signals to normative data, it is contemplated that additional information about the patient can be provided to the clinician.

For example, if comparing the Doppler ultrasound signals to normative data indicates a significant deviation from the normative data, this deviation can be quantified or qualified and presented to the clinician. Such deviations provide information to a clinician that may indicate an underlying respiratory issues, such as an undiagnosed restrictive airway disease, or the like.

As another example, in the emergency room setting, comparing the Doppler ultrasound signals to normative data can also provide information to a clinician that may indicate whether the patient is in respiratory distress. This information may help inform a clinician whether to administer emergent sedation, or may help a clinician monitor treatment provided to a patient (e.g., whether a patient has an allergic response to a treatment).

It is noted that while Doppler ultrasound signals are being acquired, additional physiological data can also be measured. For example, electrocardiograms can be recorded using ECG leads to monitor respiratory impedance and respiratory phases. Although these additional physiological data are not necessary to monitor airflow or to detect airway obstruction or respiratory compromise, they can supplement the ultrasound-based data and provide additional information to be relied upon.

Thus, the Doppler ultrasound signals are compared to baseline signal data, as indicated at step 106. Baseline signal data can be provided to the ultrasound system or to a computer system in communication with the ultrasound system for this comparison, as indicated at step 108. For example, the baseline signal data can be Doppler ultrasound signals acquired from the patient before the patient undergoes a medical procedure. That is, the baseline signal data can be acquired before the patient is administered an anesthetic agent. In some instances, the baseline signal data can include model, or normative, data corresponding to expected normal respiration for a particular patient population group, which may include Doppler ultrasound signals acquired from a different patient or subject (e.g., an age-matched, gender-matched patient). In other examples, the baseline signal data can include previously acquired portions of the Doppler ultrasound signals acquired in step 104. For instance, in a real-time monitoring application the most currently acquired Doppler ultrasound signals can be compared to Doppler ultrasound signals acquired in previous time points. As one example, a sliding window analysis could be performed, in which Doppler ultrasound signals acquired within a current time window are compared with Doppler ultrasound signals acquired outside of (i.e., prior to) the time window. In these instances, cumulative changes, or a series of changes, in the parameters of the Doppler ultrasound signals can be monitored, such that a trending change in the parameters can be identified.

As one example, the peak height of the Doppler ultrasound signals during different respiratory phases can be compared with the baseline signal data. For instance, the peak heights at inspiration, expiration, or both can be compared with baseline. In some implementations, the Doppler ultrasound signals can be Doppler spectra that indicate a velocity associated with the underlying airflow. In these instances, the height of the Doppler ultrasound signals will correspond to airflow velocities. In some other implementations, the Doppler ultrasound signals can be power Doppler signals that indicate the total strength, or amplitude, of the frequency shifts associated with the underlying airflow. In these instances, the height of the Doppler ultrasound signals will correspond to the strength of the Doppler signals caused by airflow. If a threshold change is detected, as determined at decision block 110, then an alarm can be provided to a user as indicated at step 112.

As another example, the Doppler ultrasound signals can be correlated with the baseline signal data, and portions of the Doppler ultrasound signals that correlate with the baseline signal data can be compared. As above, when changes in the correlated portions of the Doppler ultrasound signals and the baseline signal data exceed a threshold, an alarm can be provided to a user.

It is contemplated that a threshold change in the range of 20-40 percent relative to the baseline signal data can be associated with early airway compromise and, thus, can be relied upon to trigger an alarm. When using the real-time Doppler ultrasound signals as the baseline data, as described above, a lower threshold for triggering an alarm may be used since subtle or trending changes in the parameters of the Doppler ultrasound signals may be more difficult to discern than when comparing the Doppler ultrasound signals to previously acquired or normative data. A lower threshold can also be used as desired depending on the perceived risk for the particular patient. For instance, a lower threshold (e.g., 10-30 percent) may be desirable in patients with higher risk for airway obstruction or respiratory compromise.

Figure 2A:
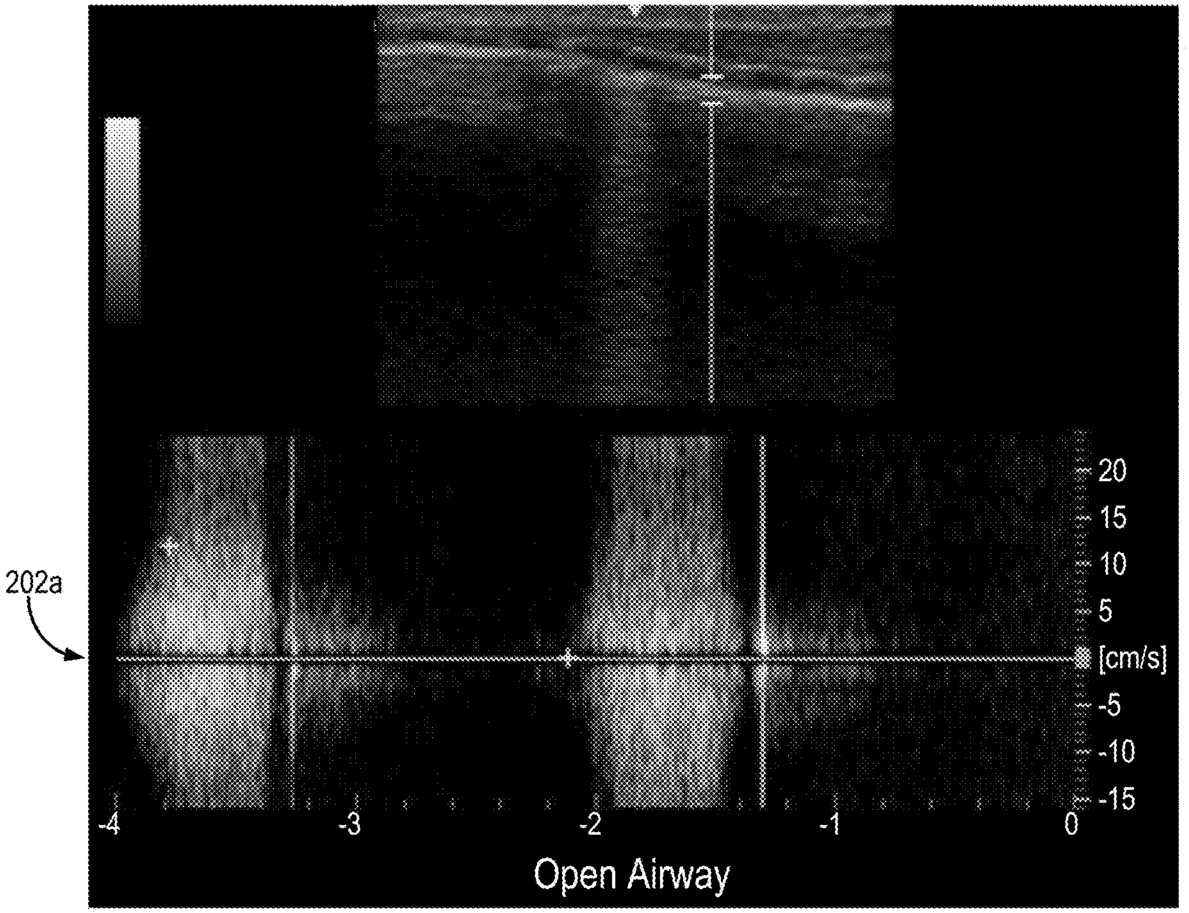
FIGS. 2A, 2B, and 2C are examples of Doppler ultrasound signals showing changes in peak amplitude and peak width in measurements from a tracheal wall, where these changes are associated with changes in airflow.
Figure 2B:
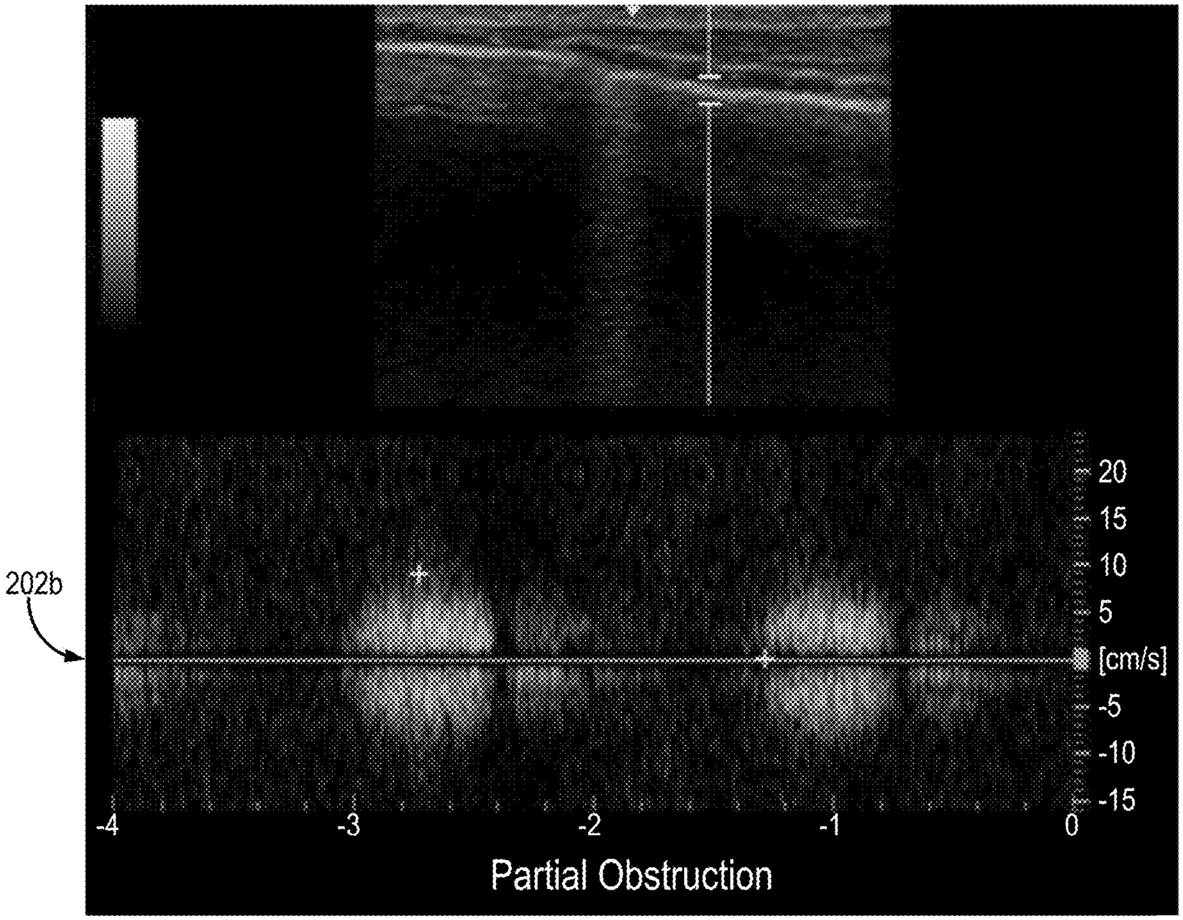
Figure 2C:
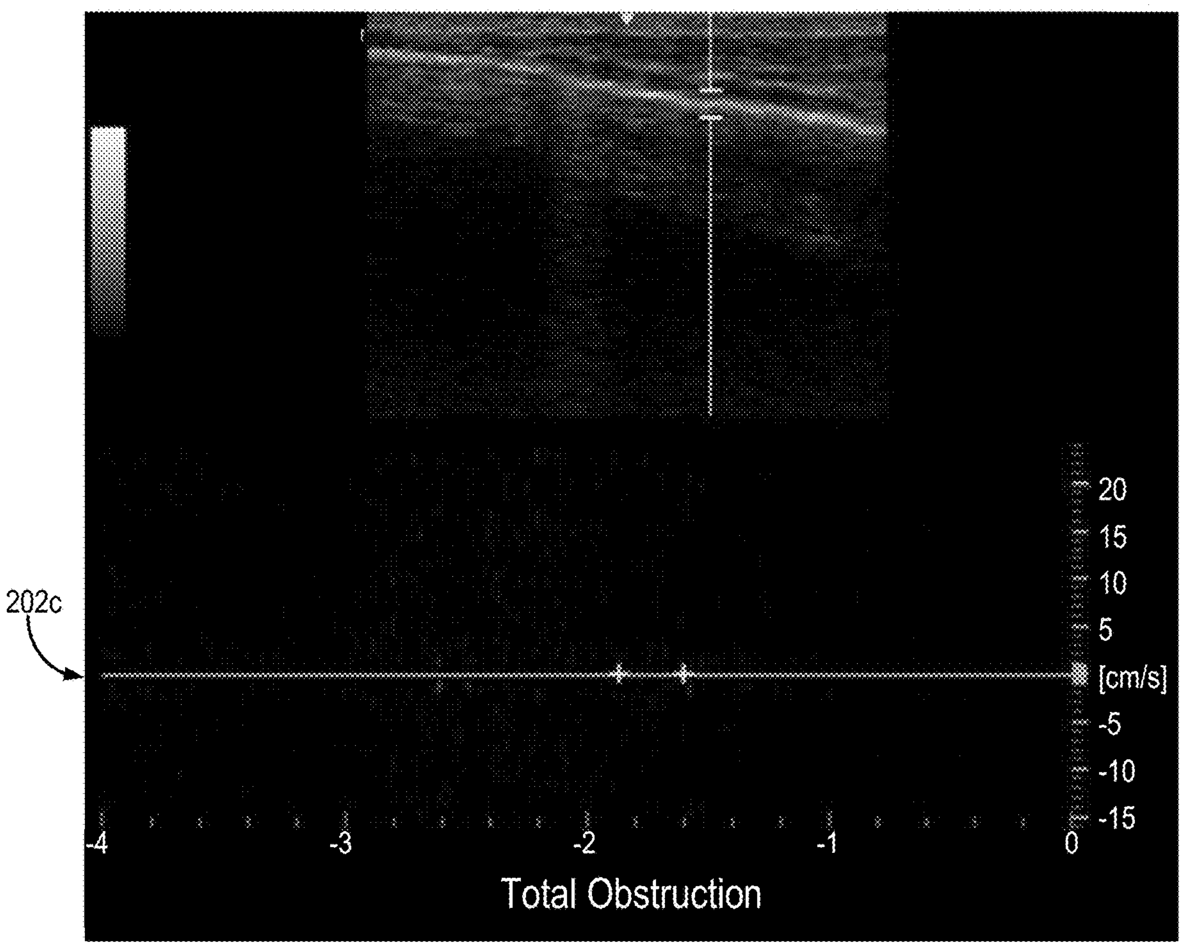

FIGS. 2A, 2B, and 2C are examples of Doppler ultrasound signals showing changes in peak amplitude and peak width measured at the tracheal wall and associated with changes in airflow. The images obtained in FIGS. 2A-2C were acquired using pulsed wave Doppler during the respiratory cycle with varying amounts of obstruction. In this experimental study, airway obstruction was mimicked using a catheter with a balloon tip that was advanced into the distal trachea of euthanized dogs via an indwelling endotracheal tube. The balloon was insufflated using predetermined volumes to create various degrees of obstruction. As seen in FIGS. 2A-2C, a progressive dampening of the Doppler ultrasound signal was observed with each gradation of airway obstruction, with total loss of signal with complete obstruction of the airway.

In these examples, the Doppler ultrasound signals include Doppler spectra 202*a*, 202*b*, 202*c* indicating frequency shifts related to the velocity associated with the underlying airflow. In the case of FIGS. 2A and 2B, the Doppler spectra 202*a* and 202*b*, respectively, indicate that a decrease in airflow is observable as a corresponding decrease in the Doppler spectra, such as a decrease in the amplitude of the Doppler spectra. In the case of FIG. 2C, the Doppler spectrum 202*c* indicates that there is no measured airflow as a result of the complete obstruction of the airway.

Figure 3A:
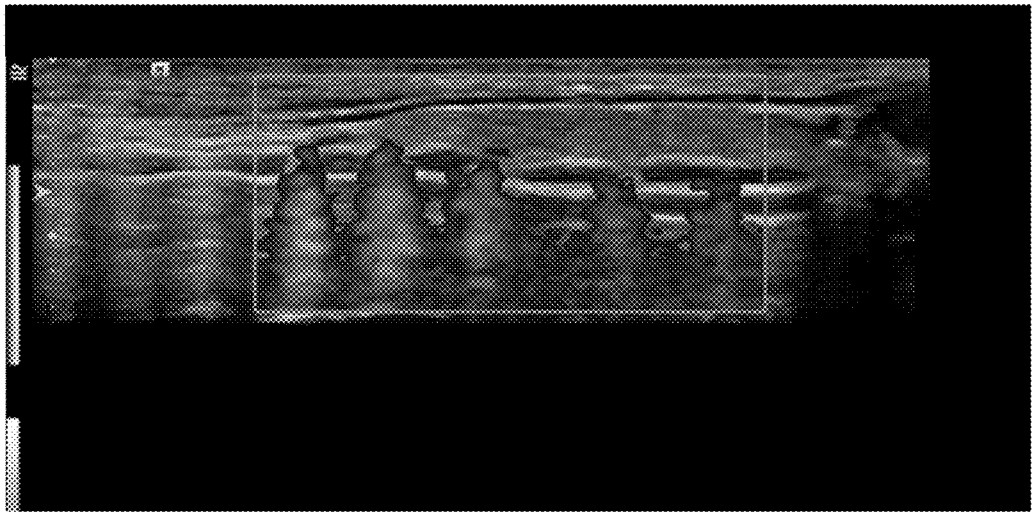
FIGS. 3A, 3B, and 3C are example of power Doppler ultrasound signals showing changes in the total strength of Doppler signal measurements from a tracheal wall, where these changes are associated with changes in airflow.
Figure 3B:
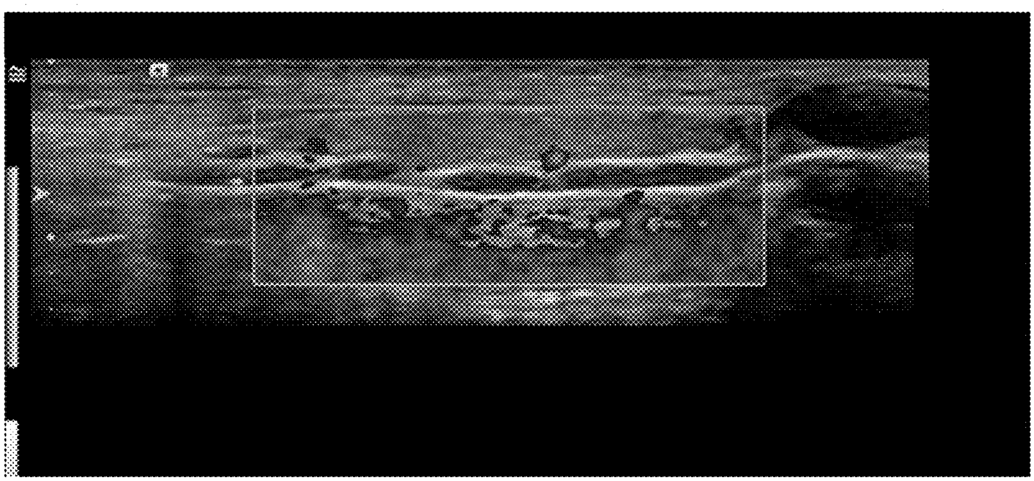
Figure 3C:
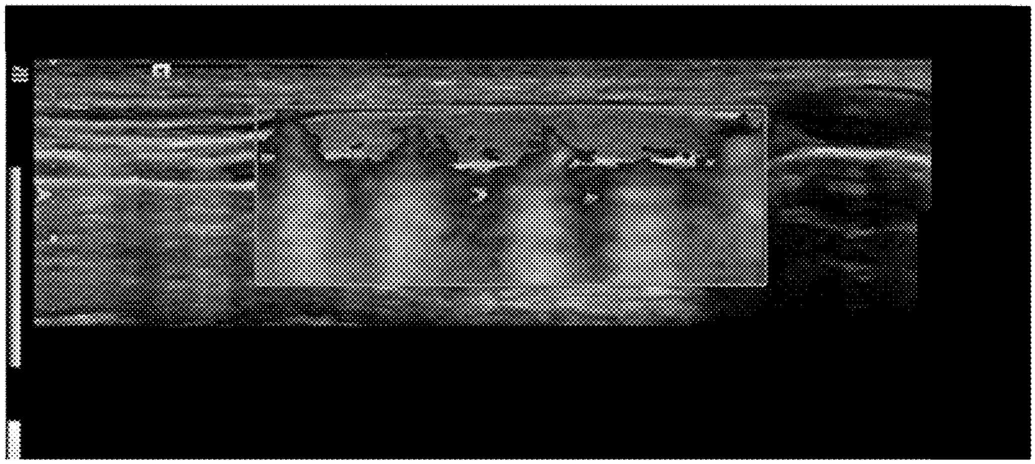

FIGS. 3A, 3B, and 3C are examples of Doppler ultrasound signals acquired with power Doppler imaging and showing changes in peak amplitude and peak width measured at the tracheal wall and associated with changes in airflow.

In addition to monitoring changes in peak heights of the Doppler ultrasound signals at one or more points during the respiratory phase, other parameters of the Doppler ultrasound signals can be measured, monitored, and compared. For example, the width of the Doppler ultrasound peaks at one or more points during the respiratory phase can be measured, monitored, and compared with similar measures in the baseline signal data.

As another example, the time between Doppler ultrasound peaks can be measured to quantify the subject's respiratory rate. By quantifying the subject's respiratory rate while also monitoring changes in the subject's airflow, the quality of each breath taken by the subject can be evaluated. For example, the number of breaths in a given time period can be quantified, while also monitoring the volume (e.g., a deep breath with good airflow versus a shallow breath with low airflow) of airflow in each breath. This information can be presented to the user in real-time to provide an additional patient monitoring tool.

As mentioned above, a determination is made while Doppler ultrasound signals are being recorded whether the comparison of the Doppler ultrasound signals with the baseline signal data satisfies one or more preselected conditions or criteria, as indicated at decision block 110. When a condition or criteria is met (e.g., a threshold change is detected), an alarm can be provided to the user, as indicated at step 112. In some instances, different alarms can be provided based on different criteria. For example, a first alarm can be provided when a first threshold is met and a second alarm can be provided when a second threshold is met. The first alarm can correspond to early airway compromise and the second alarm can correspond to complete airway obstruction. Thus, varying levels of feedback can be provided about airway obstruction or other respiratory compromise.

Figure 4:
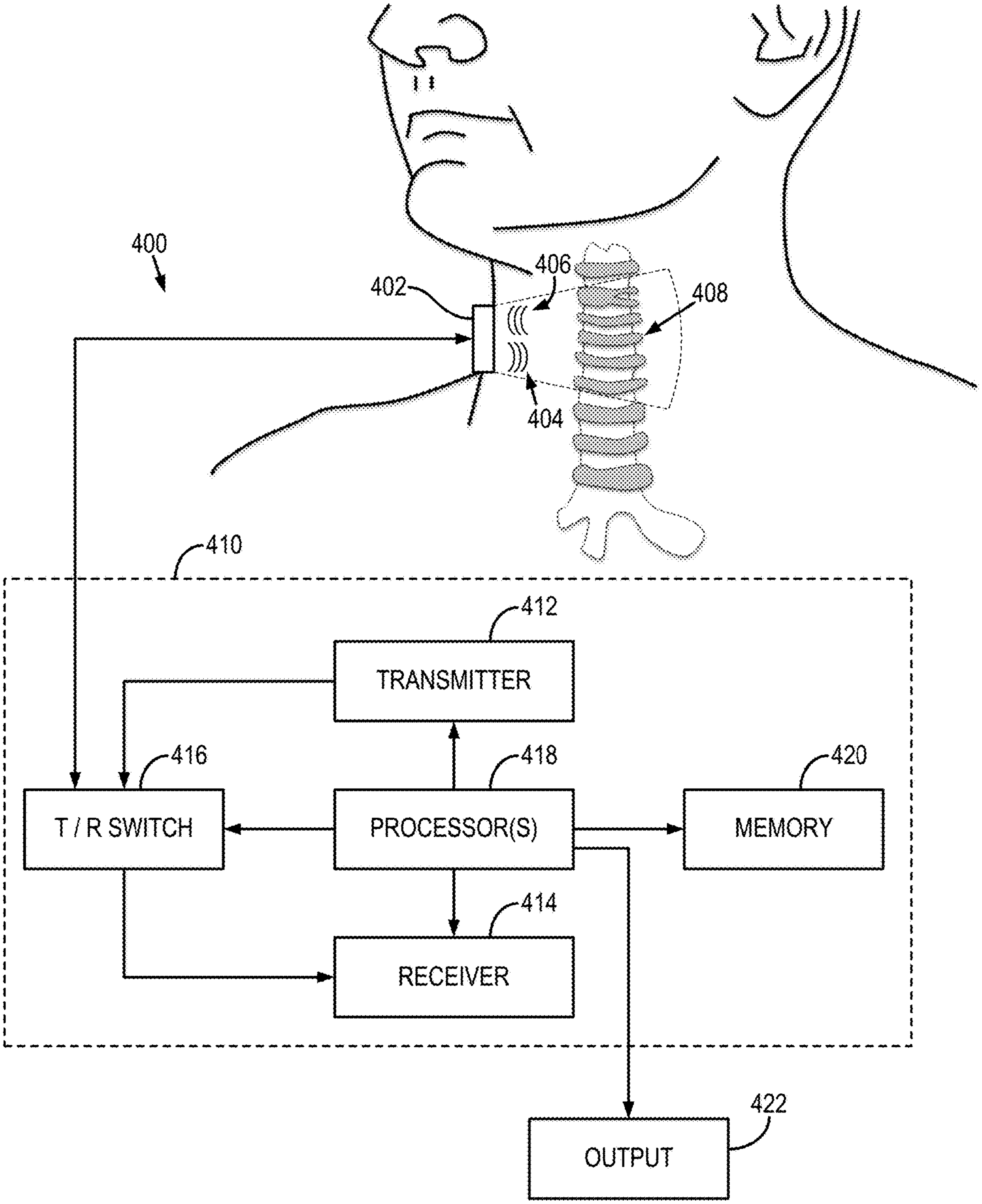
FIG. 4 is a block diagram of an example ultrasound-based airway monitor that can implement the methods described here, and can similarly be adapted for continuous monitoring of a patient's tracheal wall.

FIG. 4 illustrates the main components of an example airway monitor 400 that can implement the methods described here. In general, the airway monitor 400 can implement an ultrasound system that includes an ultrasound transducer 402 that transmits ultrasonic waves 404 and receives ultrasonic echoes 406 from a tracheal wall 408 of a patient. The ultrasound transducer 402 is generally controlled by a controller 410.

The ultrasound transducer 402 can include a plurality of separately driven transducer elements, and can include any suitable ultrasound transducer array, including linear arrays, curved arrays, phased arrays, and so on. Similarly, the ultrasound transducer 402 can include a 1D transducer, a 1.5D transducer, a 1.75D transducer, a 2D transducer, a 3D transducer, and so on.

When energized by a transmitter 412, the ultrasound transducer 402 produces a burst of ultrasonic energy (e.g., ultrasonic waves 404). The ultrasonic energy reflected back to the ultrasound transducer 412 (e.g., an echo, or ultrasonic waves 406) from the tracheal wall 408 is converted to an electrical signal (e.g., an echo signal) by the ultrasound transducer 402 and can be applied separately to a receiver 414 through a set of switches 416. The transmitter 412, receiver 414, and switches 416 are operated under the control of one or more processors 418. The transmitter 412, receiver 414, and switches 416 can be collectively referred to as an acquisition system.

The transmitter 412 can be programmed to transmit ultrasound waves for continuous wave Doppler imaging, pulsed wave Doppler imaging, or both. The receiver 414 can be programmed to implement a suitable detection sequence for the measuring Doppler shifts caused by airflow in the subject's trachea and, thus, for acquiring Doppler ultrasound signals.

In some configurations, the transmitter 412 and the receiver 414 can be programmed to implement a high frame rate. For instance, a frame rate associated with an acquisition pulse repetition frequency ("PRF") of at least 100 Hz can be implemented. In some configurations, the airway monitor 400 can sample and store at least one hundred ensembles of echo signals in the temporal direction. The airway monitor 400 can implement a detection sequence that includes one of conventional line-by-line scanning, compounding plane wave imaging, compounding diverging beam imaging, continuous wave Doppler imaging, and pulsed wave Doppler imaging.

A scan can be performed by setting the switches 416 to their transmit position, thereby directing the transmitter 412 to be turned on momentarily to energize the ultrasound transducer 402 to transmit ultrasound waves 404 to the tracheal wall 408. The switches 416 can then be set to their receive position and the subsequent echo signals produced by the ultrasound transducer 402 in response to one or more detected echoes (e.g., ultrasound waves 406) are measured and applied to the receiver 414. The separate echo signals from the transducer elements in the ultrasound transducer 402 can be combined in the receiver 414 to produce a single echo signal.

The echo signals (e.g., Doppler ultrasound signals) are communicated to one or more processors 418 to process Doppler ultrasound signals or images generated from such signals. As an example, the one or more processor 418 can process the Doppler ultrasound signals to can be programmed to implement the methods described in the present disclosure for generating images that depict the tracheal wall 408 of the patient, for measuring parameters of Doppler ultrasound signals recorded from the tracheal wall 408 of the patient, and for comparing those parameters with similar parameters from baseline signal data provided to the one or more processors 418. In some implementations, the one or more processors 418 can perform power Doppler analyses, such as by generating power Doppler signals (e.g., total strength or amplitude of the measured Doppler signals) from the acquired ultrasound signals. The one or more processors 418 can be in communication with a memory 420 that contains the baseline data described above, and which can store Doppler ultrasound signals acquired by the airway monitor 400 and other suitable data.

The output from the one or more processors 418 can be provided to an output 422, which can include a display, speaker, or both. For instance, the output 422 can include an alarm, which may be a display for generating a visual alarm, or a speaker for generating an auditory alarm. In some examples, images produced from the Doppler ultrasound signals by the one or more processor 418 can be displayed on an output 422 that includes a display.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for monitoring airflow in a trachea using an ultrasound system, the method comprising:

(a) selecting a region-of-interest in a subject that includes a tracheal wall of the subject;

(b) acquiring Doppler ultrasound signals from the tracheal wall;

(c) generating a quantitative measure of airflow in the trachea of the subject by processing the Doppler ultrasound signals acquired from the trachea wall using a computer system; and (d) outputting the quantitative measure of airflow in the subject's trachea using the computer system.

2. The method of claim 1, wherein the Doppler ultrasound signals are acquired in a longitudinal plane relative to the tracheal wall.

3. The method of claim 1, wherein the quantitative measure of airflow in the trachea comprises a respiratory rate estimated from the Doppler ultrasound signals acquired from the tracheal wall.

4. The method of claim 3, wherein the respiratory rate is estimated by identifying peaks in the Doppler ultrasound signals and determining the respiratory rate based on the peaks in the Doppler ultrasound signals.

5. The method of claim 1, wherein the quantitative measure of airflow comprises changes in tissue Doppler velocities measured from the Doppler ultrasound signals acquired from the tracheal wall.

6. The method as recited in claim 1, wherein the Doppler ultrasound signals acquired from the tracheal wall comprise Doppler spectra indicating velocity data associated with airflow in the trachea.

7. The method as recited in claim 1, wherein the Doppler ultrasound signals acquired from the tracheal wall include power Doppler signals indicating amplitude data associated with airflow in the trachea.

8. The method as recited in claim 1, wherein the Doppler ultrasound signals are acquired using pulsed wave Doppler imaging.

9. The method as recited in claim 1, wherein the Doppler ultrasound signals are acquired using continuous wave Doppler imaging.

* * * * *